United States Patent [19]

Macri

[11] Patent Number: 5,316,953
[45] Date of Patent: May 31, 1994

[54] SCREENING METHOD FOR DETECTING FETAL CHROMOSAL ABNORMALITIES

[76] Inventor: James N. Macri, 170 Sidney St., Oyster Bay, N.Y. 11771

[21] Appl. No.: 868,160

[22] Filed: Apr. 14, 1992

Related U.S. Application Data

[63] Continuation-in-part of Ser. No. 360,603, Jun. 1, 1989, abandoned, which is a continuation-in-part of Ser. No. 349,373, May 8, 1989, abandoned, which is a continuation-in-part of Ser. No. 311,808, Feb. 17, 1989, abandoned, which is a continuation-in-part of Ser. No. 297,481, Jan. 17, 1989, abandoned.

[51] Int. Cl.$^5$ .................. G01N 33/49; G01N 33/493
[52] U.S. Cl. .................................. 436/87; 435/7.9; 435/7.92; 436/65; 436/86; 436/510; 436/518; 436/548
[58] Field of Search ............... 436/501, 510, 518, 817, 436/818, 87, 86; 435/7.92

[56] References Cited

PUBLICATIONS

Arab et al–Biological Abstracts Report of Meeting 12-15 Oct. 1988, New Orleans, La. (39th Annual Meeting of Am. Soc. of Human Genetics).

*Primary Examiner*—Sam Rosen
*Attorney, Agent, or Firm*—Kenyon & Kenyon

[57] ABSTRACT

A screening method for fetal Down syndrome using free beta (HCG) as a marker. The maternal blood level of free beta (HCG) is measured and compared to reference data, at a similar gestational age, of the level of free beta (HCG) in pregnant women carrying a fetus with Down syndrome and pregnant women carrying an unaffected fetus. The method may advantageously be utilized during the first and second trimesters of pregnancy. Fragments of free beta and "nicked" free beta may also be utilized as markers.

7 Claims, 15 Drawing Sheets

| MARKER | P VALVE |
|---|---|
| U E (EIA) | .14 |
| U E (RIA) | .66 |
| INTACT hCG | .0002 |
| AFP | .0365 |
| INTACT+ $\beta$ hCG | <.0001 |

FIG. 1

| ANALYTES | FALSE POSITIVE | DETECTION EFFICIENCY | CONTROLS/ AFFECTED |
|---|---|---|---|
| U E (RIA) | 2.4 | 15.4 | 495/26 |
| U E (EIA) | 4.4 | 10.3 | 520/29 |
| LOG INTACT hCG | 7.4 | 33.3 | 489/27 |
| LOG AFP | 5.0 | 26.9 | 424/26 |
| LOG INTACT+ $\beta$ hCG | 9.6 | 56.0 | 437/25 |

FIG. 2

| ANALYTES | FALSE POSITIVE | DETECTION EFFICIENCY | CONTROLS/ AFFECTED |
|---|---|---|---|
| 1 LOG AFP<br>LOG INTACT+ β hCG<br>U E | 8.5 | 64.0 | 422/25 |
| 2 LOG AFP<br>LOG INTACT hCG<br>U E | 8.4 | 57.7 | 419/26 |

FIG. 3

| PERCENTILE OF UNAFFECTED PREGNANCIES | DOWN SYNDROME CASES |
|---|---|
| > 5 | 98 |
| >10 | 98 |
| >25 | 90 |
| >50 | 86 |
| >75 | 79 |
| >90 | 62 |
| >95 | 36 |
| >99 | 31 |

FIG. 4

| ANALYTE | FALSE POSITIVE | DETECTION EFFICIENCY | CONTROLS/ AFFECTED |
|---|---|---|---|
| LOG β SUBUNIT | 5.2 | 65.4 | 154/26 |
| LOG α SUBUNIT | 0.0 | 0.0 | 157/17 |

FIG. 5

| GESTAGIONAL AGE RANGE | FALSE POSITIVE | DETECTION EFFICIENCY | CONTROLS/ AFFECTED |
|---|---|---|---|
| ALL WEEKS | 3.2 | 73.1 | 154/26 |
| < 17 WEEKS | 3.8 | 83.3 | 79/18 |
| >= 17 WEEKS | 1.3 | 50.0 | 75/8 |

FIG. 6

| RISK CUT-OFF | FALSE POSITIVE | DETECTION EFFICIENCY |
|---|---|---|
| 1 IN 400 | 5.0 | 80 |
| 1 IN 350 | 4.2 | 76 |
| 1 IN 300 | 3.5 | 73 |
| 1 IN 250 | 2.6 | 67 |
| 1 IN 200 | 1.6 | 60 |
| 1 IN 150 | 0.9 | 55 |
| 1 IN 100 | 0.5 | 45 |

FIG. 7

TABLE 8

| MARKER(S) | FALSE POS. RATE(%) | SENSITIVITY (%) |
|---|---|---|
| FREE $\beta$ (NO LOG, NO GA) | 5.7 | 69.2 |
| LOG FREE $\beta$ (NO GA) | 5.9 | 69.2 |
| FREE $\beta$, GA | 5.7 | 69.2 |
| LOG FREE $\beta$, AFP IN LOG MOMs | 3.9 | 73.1 |
| FREE $\beta$, AFP IN LOG MOMs | 1.3 | 73.1 |
| FREE $\beta$, GA, LOG AFP | 5.2 | 73.1 |
| FREE $\beta$, LOG AFP | 1.3 | 73.1 |
| FREE $\beta$ IN LOG MOMs, AFP IN LOG MOMs | 3.9 | 69.2 |
| LOG FREE $\beta$, LOG AFP | 3.3 | 69.2 |
| LOG AFP, LOG INTACT+ $\beta$, LOG $\alpha$, GA | 9.6 | 52.9 |
| LOG INTACT hCG, GA, LOG INTACT+ $\beta$, LOG $\alpha$ | 26.1 | 52.9 |
| LOG AFP, LOG INTACT hCG, GA, LOG INTACT+ $\beta$, LOG $\alpha$ | 20.4 | 52.9 |

FIG. 10

SCREENING METHOD FOR DETECTING FETAL CHROMOSAL ABNORMALITIES

This application is a continuation-in-part of application Ser. No. 07/360,603, filed Jun. 1, 1989, which is a continuation-in-part of application Ser. No. 07/349,373, filed May 8, 1989, which is a continuation-in-part of application Ser. No. 07/311,808 filed Feb. 17, 1989 which is a continuation-in-part of application Ser. No. 07/297,481, filed Jan. 17, 1989.

BACKGROUND OF THE INVENTION

The present invention relates to a method for detecting fetal Down syndrome (Trisomy 21) during prenatal screening. This method also relates to other more rare but detectable chromosomal trisomies such as Trisomy 13 and Trisomy 18. More particularly the present invention relates to a method for improving detection efficiency in screening for Down syndrome by measuring the amount of the free beta subunit of human chorionic gonadotropin (hCG) in the blood of pregnant women.

Down syndrome, also referred to as Trisomy 21, is the most common congenital cause of severe mental retardation Generally, fetal Down syndrome can be determined by a diagnostic procedure including amniocentesis and karyotyping. However, this diagnostic procedure is invasive and involves risk to the woman and the fetus. Amniocentesis and karyotyping are not routinely performed during all pregnancies. Instead, one or more screening methods may be utilized to determine when the risk to the pregnancy warrants the risk of undergoing an invasive diagnostic procedure.

The incidence of Down syndrome increases significantly with increasing maternal age. Historically, the prenatal search for Down syndrome has focused on pregnant women at and over the age of 35, at which ages the risks of Down syndrome approach or exceed the risks of diagnostic procedures utilized to detect fetal Down syndrome. Therefore the standard method of prenatal screening has involved selecting women for diagnostic amniocentesis on the basis of maternal age. Age, however, is an inadequate screening criterion in that only about 20% of all Down syndrome pregnancies can be detected by carrying out amniocentesis and karyotyping on the 5% of pregnant women most at risk, that is, those aged 35 years or greater. And, because in actual clinical practice only about half of the women aged 35 years or greater undergo amniocentesis and karyotyping, fewer than 10% of Down syndrome pregnancies are prenatally detected.

In 1984 an association between lowered maternal blood alpha-fetoprotein (AFP) levels and fetal Down syndrome was discovered. For example, see "An association between low maternal serum alpha-fetoprotein and fetal chromosomal abnormalities"; Merkatz, Macri, et al.; Am. J. Obstet. Gynecol. 148:886, 1984; the disclosure of which is hereby incorporated by reference. In this publication it was noted that other chromosomal trisomies, in particular Trisomy 13 and Trisomy 18, were also associated with lowered maternal blood AFP levels The incidence of these additional chromosomal trisomies (1 in 5000 pregnancies and 1 in 6600 pregnancies, respectively) is significantly lower than the general a priori risk associated with Trisomy 21 (Down syndrome). However, because of the association of these other chromsomal trisomies with lowered MSAFP levels, such abnormalities will also be detected within a screening protocol utilizing maternal blood AFP and the free beta subunit of hCG and possibly additional markers described herein. It is obvious to those skilled in the art that in using the protocol described herein for Trisomy 21, the detection of Trisomy 13 and 18 may also be accomplished. The association between lowered maternal blood AFP levels and fetal Down syndrome presented the opportunity to use a non-invasive blood screening test in the detection of Down syndrome cases in young, apparently unaffected families where approximately 80% of Down syndrome cases occur. It is estimated that the use of a screening test based on low maternal blood AFP (as a screening marker) would lead to the prenatal detection of approximately 20% of all cases of fetal Down syndrome.

Another method for screening involves measuring the level of unconjugated estriol (UE) in maternal blood. For example, see "Maternal blood screening for Down syndrome in early pregnancy"; Wald, et al. British Journal of Obstetrics and Gynocology (BMJ) Volume 95, April 1988, the disclosure of which is hereby incorporated by reference. The measurement of UE however, provides a poor basis for screening.

More recently an association between elevated maternal blood hCG levels, elevated maternal blood level of the alpha subunit of hCG (hCG is composed of two subunits, hereinafter referred to as alpha-hCG and beta-hCG respectively), and fetal Down syndrome was discovered. For example, see "Abnormal Maternal Serum Chorionic Gonadotropin Levels in Pregnancies with Fetal Chromosome Abnormalities"; Bogart, Pandian and Jones; Prenatal Diagnosis, Vol. 7, 623–630 (1987) the disclosure of which is hereby incorporated by reference. In the Bogart article it is estimated that the use of elevated maternal blood hCG levels and elevated maternal blood levels of the alpha subunit of hCG, would detect approximately 68% of the chromosomally abnormal fetuses. However, these results were obtained from a study on pregnancies at 18–25 weeks of gestation and the affected cases appear to be of women previously identified as being at risk for Down syndrome.

Generally, as suggested above, screening by evaluation of maternal blood hCG has involved only the measurement of hCG in general and additionally the measurement of alpha-hCG. Although these screening methods do detect fetal Down syndrome, there is a need and a desire for a method which detects a greater percentage of fetal Down syndrome cases.

I have discovered a previously unknown association between elevated levels of maternal blood free beta-hCG and fetal Down syndrome. I have also discovered a previously unknown association between the maternal blood level of free beta-hCG and the maternal blood level of AFP and fetal Down syndrome, I have further discovered a previously unknown association between the ratio of the maternal blood level of free beta-hCG to the maternal blood level of the intact hCG molecule and fetal Down syndrome. I have still further discovered that using a multivariate discriminant analysis technique improves the detection efficiency of a screening method using the maternal blood level of free beta-hCG, or the maternal blood level of free beta-hCG and the maternal blood level of AFP, or the log of either, or the log of both, especially when gestational age is also incorporated as a variable in the discriminant analysis technique, for a chosen risk cut-off level. Gestational age refers to the age of the pregnant woman's fetus. Detection efficiency refers to the percentage of cases of fetal Down syndrome which are correctly detected for a chosen risk cut off level. The risk cut off level will be more fully explained in a following section. Discriminant analysis is a generally known approach to multivariate analysis involving the separation of a population into two or more groups by a univariate risk assessment. Discriminant analysis is also sometimes described as a way of constructing a linear combination of independent variables, thus reducing the problem of measuring group differences to a univariate problem. Discriminant analysis can also be performed when there is only one variable involved in a problem. A general discussion of discriminant analysis can be found in Marketing Research; Churchill, G. A.; Dryden, 1976; Chapter 15, pages 530–543, the disclosure of which is hereby incorporated by reference. I have discovered that subjecting the maternal blood levels of free beta-hCG, the maternal blood levels of intact hCG, the ratio of the maternal blood level of free beta-hCG to the maternal blood level of the intact hCG molecule, the maternal blood level of AFP, the maternal blood level of UE, and gestational age to multi-variate discriminant analysis detects a greater percentage, with a lower false positive rate, of fetal Down syndrome cases than any other known screening method for the prenatal detection of Down syndrome. I have further discovered that a still greater number of the cases of fetal Down syndrome may be detected by using only the measurements of the maternal blood levels of free-beta hCG and the maternal blood levels of AFP and subjecting the log of each measurement and gestational age to a multivariate discriminant analysis. These and other discoveries will be more fully explained in the Summary of the Invention section and the Detailed Description of the Invention section.

One object of the present invention is to provide a method and process for screening for fetal Down syndrome which detects a greater percentage of fetal Down syndrome cases with a given false positive rate than other known prenatal screening methods.

Another object of the present invention is to provide a method and process for screening for fetal Down syndrome which has a lesser false positive rate for a given detection percentage than other known methods.

A still further object of the present invention is to apply multi-variate discriminant analysis to methods for screening for Down syndrome to detect a greater percentage of u fetal Down syndrome cases with a lesser false positive rate.

A further object of the present invention is to provide a method and process for screening for fetal Down syndrome by measuring the level of maternal blood free beta-hCG.

A still further object of the present invention is to provide a method and process for screening for fetal Down syndrome by measuring the maternal blood level of AFP and the maternal blood level of free beta-hCG.

Other objects and advantages of the present invention will become apparent in the following description of the invention.

SUMMARY OF THE INVENTION

To achieve these and other objects, according to the present invention a pregnant woman's (hereinafter the patient) maternal serum levels of free beta-hCG are measured by conventional immunological methods which can include immunoassay techniques such as those referred to in the papers above, and other techniques known in the art. The level of free beta-hCG is then compared to a set of reference data to determine the patient's risk of carrying a fetus with Down syndrome. To improve detection efficiency, the level of free beta-hCG and the gestational age can be compared to a set of reference data. To further improve detection efficiency, a patient's maternal blood levels of free beta-hCG and AFP (referred to as "markers") are measured by conventional immunological methods, including assay techniques known to the art such as those referred to in the papers above. The levels of each marker are then compared to a set of reference data to determine the patient's risk of carrying a fetus with Down syndrome. A multivariate discriminant analysis technique is used to compare the levels of the markers to a set of reference data. More particularly, a patient specific risk is then calculated using Bayes rule, the patient's a priori risk, and the relative frequencies for unaffected and affected pregnancies which are determined by incorporating the log of the patient's quantitative levels of each marker into the probability density functions for the reference data developed using multivariate discriminant analysis. If the patient's risk of carrying a fetus with Down syndrome is greater than a given risk cut-off level, the patient should be counseled about further diagnostic tests to confirm the presence of Down syndrome. Incorporating gestational age as a marker along with the level of free beta-hCG and the maternal blood level of AFP will further improve detection efficiency. Since the maternal blood level of free beta-hCG and the maternal blood level of AFP for a number of samples tend to be distributed according to a log-gaussian distribution curve, the greatest detection efficiency can be achieved by incorporating the log of the patient's quantitative levels of each marker and gestational age into the probability density functions for the reference data developed using multivariate discriminant analysis.

An advantage of the method and process of the present invention is that it correctly predicts a higher percentage of fetal Down syndrome cases, with a lesser false positive rate than other known methods and processes.

Other advantages of the present invention will become clear from the following more detailed description and the following examples.

BRIEF DESCRIPTION OF THE DRAWINGS

FIG. 1 is a Table, referred to in Example 2, showing the level of significance of individual markers for Trisomy 21.

FIG. 2 is a table, referred to in Example 2, showing Down syndrome screening efficiency of individual markers.

FIG. 3 is a table, referred to in Example 2, showing Down syndrome screening efficiency of composite markers.

FIG. 4 is a table, referred to in Example 2, showing proportion of Down syndrome cases above given percentiles of the distribution of free beta subunit of hCG in unaffected pregnancies.

FIG. 5 is a table, referred to in Example 2, showing Down syndrome efficiency of individual markers.

FIG. 6 is a table, referred to in Example 2, showing Down syndrome screening efficiency of log AFP and log free beta subunit of hCG as a composite marker at different gestational age ranges.

FIG. 7 is a table, referred to in Example 2, showing projected Down syndrome screening efficiency of AFP, free beta-hCG and maternal age across the U.S.A.

FIG. 10, is a Table, referred to in Example 3, showing Down syndrome screening efficiency for a variety of combinations of markers.

DETAILED DESCRIPTION OF THE INVENTION

Figure 8:
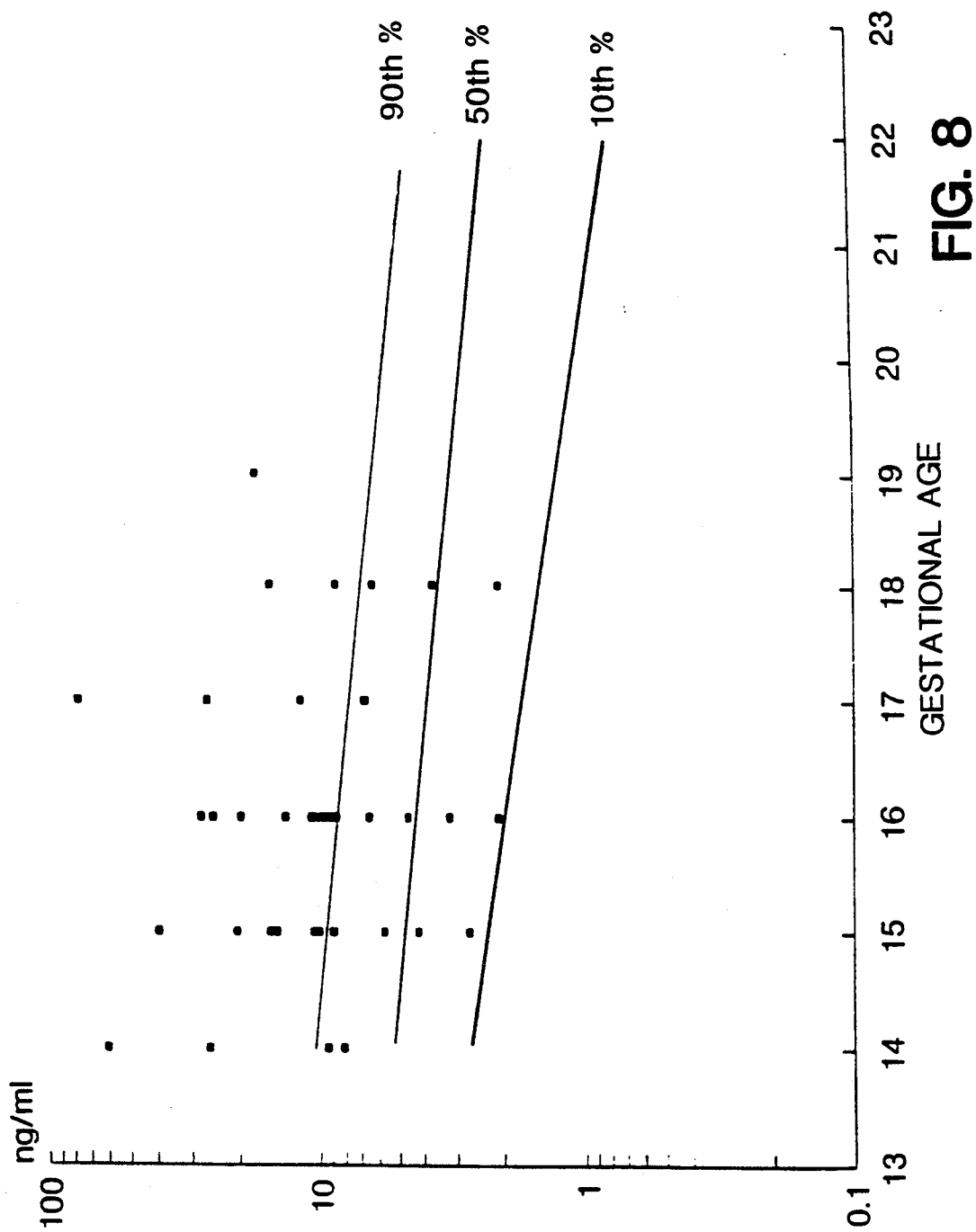
FIG. 8, referred to in Example 2, shows the levels or free beta subunit of hCG in cases of trisomy 21 in relation to various percentiles of the unaffected pregnancies.

In one embodiment of the present invention, a maternal blood sample is taken from a patient. The maternal blood level of free beta-hCG is then measured by conventional analytical methods, such as immunological methods known to the art. The maternal blood level of free beta-hCG is then compared to a set of reference data to determine whether the patient is at an increased risk of carrying a fetus with Down syndrome. To increase detection efficiency, gestational age and the maternal blood level of free beta-hCG may be compared to a set of reference data to determine whether the patient is at increased risk of carrying a fetus with Down syndrome.

Although any of the known analytical methods for measuring the maternal blood level of free beta-hCG will function in the present invention, as obvious to one skilled in the art, the analytical method used for free beta-hCG must be the same method used to generate the reference data for free beta- hCG. If a new analytical method is used for free beta-hCG, a new set of reference data, based on data developed with the method, must be generated.

It is also generally understood that in generating monoclonal antibodies specific for the beta-chain of hCG, some antibodies will be specific for the protein and some will be specific for carbohydrate associated antigenic sites. The measurement of the level of free beta-hCG referred to throughout the description of the invention includes using antibodies specific for either the protein or the carbohydrate associated antigenic sites or any other site on free beta-hCG.

It is further understood by those of ordinary skill in the art, that while the free alpha subunit of hCG is encoded by a single gene, the free beta subunit is encoded by a complex family of at least seven very similar genes or pseudogenes. For example, see "Human chorionic gonadotropin beta-subunit is encoded by at least eight genes arranged in tandem and inverted pairs," Boorstein, Vamvakopoules, & Fiddes; Nature Vol 300, 2 December 1982; the teaching of which is hereby incorporated by reference. It is known that only three of the seven free beta hCG genes are expressed in the normal placental production of free beta hCG. For example, see "Fragmentation of the Beta-Subunit of Human Chorionic Gonadotropin Produced by Choriocarcinoma"; Nishimura, Ide, Utsunomiya, Kitajima, Yuki, and Mochizuki; Endocrinology, Vol. 123, No. 1, 1988; the teachings of which are hereby incorporated by reference. Whether these same three genes are expressed in disease states, such as during the presence of fetal Down syndrome, has not been determined. It is, therefore, possible that multiple forms of free beta hCG with small differences in amino acid sequences, or other small differences, may be synthesized. It is further possible that in Down syndrome, one or more of the free beta hCG genes are expressed, thereby producing a unique variant or variants of free beta hCG. According to the present invention these variants, if they exist, are measured by conventional immunological techniques for measuring free beta hCG. An assay produced to measure the specific free beta hCG variant, or variants, associated with Down syndrome, if any, may result in even further enhancement of detection efficiency.

We have effectively used monoclonal antibody assay techniques to measure the free beta subunit of hCG to distinguish between Trisomy 21 affected and unaffected pregnancies. Detection efficiency for Trisomy 21 as high as 83% has been achieved. As is well known to those skilled in the art, the use of antibodies to quantitate specific analytes may result in degrees of cross-reactivity with a distinct yet similar substance. Hence, the distinction between affected and unaffected cases may be due to the presence of a distinct form of the free beta subunit of hCG which, because of some degree of cross-reactivity with the antibodies being used, is being detected. If such an aberrant form of the free beta subunit of hCG is identified, it may be designed as a new biochemical substance. Indeed, information from the scientific literature indicates that aberrant forms of beta hCG have been recognized (for example, see Nishimura et al. infra.)

Trisomy 21 affected cases may also be characterized by an aberrant form of the free beta subunit of hCG. If form of the free beta subunit of hCG, those skilled in the art will be capable of developing specific antibodies to such aberrant forms which may result in a further enhancement of detection efficiency for this syndrome.

One such aberrant or alternative form of free beta (HCG) may be referred to as "nicked" free beta. In nicked free beta peptide linkages are missing between amino acids in the free beta. In known forms of nicked free beta, peptide linkages can be missing between residues 44 and 45 or between residues 47 and 48. Techniques have been developed to measure forms of nicked free beta. As explained above, these techniques may be utilized in the method of the present invention to screen for fetal Down syndrome by measuring the maternal blood level of nicked free beta.

The reference data reflects the maternal blood level of free beta-hCG for pregnant women carrying fetuses with Down syndrome (also referred to as "affected") and/or the maternal blood level of free beta-hCG for pregnant women carrying normal fetuses (also referred to as "unaffected"). As will be generally understood by those of skill in the art, methods for making by comparison. For any decision making process, reference values based on patients having the disease or condition of interest and/or patients not having the disease or condition of interest are needed. In the present invention the reference values are the maternal blood level of the measured marker or markers, for example, free beta-hCG, in both pregnant women carrying Down syndrome fetuses and pregnant women carrying normal fetuses A set of reference data is established by collecting the reference values for a number of samples. As will be obvious to those of skill in the art, the set of reference data will improve by including increasing numbers of reference values.

To determine whether the patient is at increased risk of carrying a fetus with Down syndrome, a cut-off must be established. It is obvious to those skilled in the art that cut-off established to determine whether a patient is at increased risk of carrying a fetus with Trisomy 13 or Trisomy 18 may also be effective in identifying cases of trisomy 21. This cut-off may be established by the laboratory, the physician or on a case by case basis by each patient. The cut-off level can be based on several criteria including the number of women who would go on for further invasive diagnostic testing, the average risk of carrying a Down syndrome fetus or all the women who go on for further invasive diagnostic testing, a decision that any woman whose patient specific risk is greater than a certain risk level such as 1 in 400 should go on for further invasive diagnostic testing or other criteria known to those skilled in the art. The cut-off level could be established using a number of methods, including: percentiles, mean plus or minus standard deviation(s); multiples of median value; patient specific risk or other methods known to those who are skilled in the art.

In another embodiment of the present invention, which results in a detection of a greater number of the cases of fetal Down syndrome, a maternal blood sample is taken from a patient. The maternal blood levels of the intact hCG molecule, free beta-hCG, UE and AFP (hereinafter referred to as "markers") are then measured by conventional analytical methods, such as immunological methods known to the art. Although any of the known analytical methods for measuring the maternal blood levels of these markers will function in the present invention, as obvious to one skilled in the art, the analytical method used for each marker must be the same method used to generate the reference data for the particular marker. If a new analytical method is used for a particular marker, a new set of reference data, based on data developed with the method, must be generated.

A patient specific risk of carrying a fetus with Down syndrome is then calculated using Bayes rule, the patient's a priori risk, and the relative frequencies for unaffected and affected pregnancies which are determined by incorporating the patient's quantitative levels on each marker (the intact hCG molecule, free beta-hCG, UE and AFP) and the ratio of free beta-hCG to the level of the intact hCG molecule, along with the patient's gestational age, into the probability density functions developed for the reference data using multivariate discriminant analysis. The multivariate discriminant analysis can be performed on the commercially available computer program statistical package Statistical Analysis System (manufactured and sold by SAS Institute Inc.) or by other methods of multivariate statistical analysis or other statistical software packages known to those skilled in the art.

The probability density function provides a method for comparing the patient's level on each marker to a set of reference data. One type of probability density function is set forth below, although as will be obvious to one skilled in the art, other probability density functions will perform similarly, and therefore perform adequately in the present invention.

Formula for Risk of Down syndrome $$\frac{(1/\sqrt{|COV|})EXP(-.5(Xa - Ma)^T cov^{-1}(Xa - Ma)) \times \text{Prior Risk}}{[(1/\sqrt{|COV|})\ EXP(-.5(Xa - Ma)^T cov^{-1}(Xa - Ma)) * \text{Prior Risk} + (1/\sqrt{|COV|})\ EXP(-.5(Xu - Mu)^T cov^{-1}(Xu - Mu) * (1 - \text{Prior Risk})]}$$

The subscript "a" refers to the affected cases
The subscript "u" refers to the unaffected cases
(X−M) is a vector where each element is the level of each variable minus the mean of the variable.
$cov^{-1}$ is the inverse of the pooled covariance matrix of the affected and unaffecteds of all of the variables in the model (X−M) is the transpose of the (X-M) vector.
EXP refers to the exponential function.
COV refers to the determinant of the covariance matrix of all the variables in the model for the reference data.

As obvious to those skilled in the art, individual covariance matrices for unaffected and affected pregnancies can be substituted for the pooled covariance matrix. The formula for the Risk of Down syndrome would then become:

$$\frac{(1/\sqrt{|COVa|})EXP(-.5(Xa - Ma)^T COVa^{-1}(Xa - Ma)) \times \text{Prior Risk}}{[(1/\sqrt{|COVa|})\ EXP(-.5(Xa - Ma)^T COVa^{-1}(Xa - Ma)) * \text{Prior Risk} + (1/\sqrt{|COVu|})\ EXP(-.5(Xu - Mu)^T COVu^{-1}(Xu - Mu) * (1 - \text{Prior Risk})]}$$

COV refers to the determinant of the covariance matrix of all the variables in the model for the reference data.

For the purposes of the discriminant analysis an assumption is made as to the prior probability of Down syndrome in the general unselected population. Generally, the prior probability is approximately 1 in 800. For the multivariate discriminant analysis a decision is made as to what risk cut-off level constitutes a positive test result. For example, if it is desirable to perform further diagnostic tests on a pregnant woman who has a 1 in 400 or greater possibility of carrying a Down syndrome fetus, then when the results of the discriminant analysis indicate that a pregnant woman has a 1 in 400 or greater possibility of carrying a Down syndrome fetus, the pregnant woman is considered to have a positive test result. If a positive test result is indicated, the patient should be counseled about further diagnostic tests to confirm the presence of Down syndrome.

With reference to FIGS. 11-14, the apparatus and a flowchart for a computer program for calculating the reference parameters and specific risk are shown.

Figure 11:
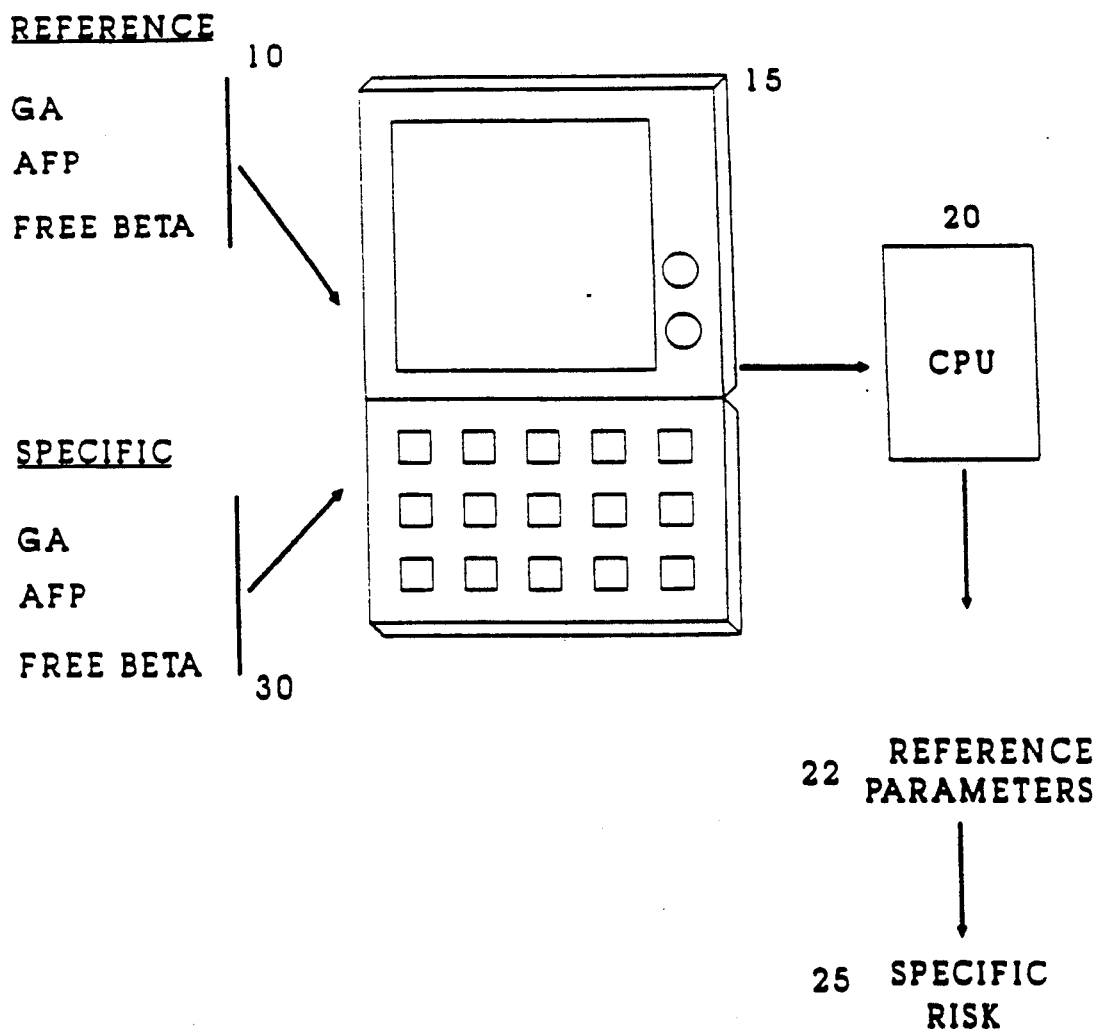
FIG. 11 shows the apparatus of the present invention utilized in performing the method for detecting Down syndrome.

As shown in FIG. 11, the gestational age GA, the level of AFP and the level of free beta hCG are determined by conventional techniques from affected and unaffected pregnancies in order to develop reference data. A large number of samples are chosen to increase reliability. The measurements for the development of reference parameters are indicated schematically at 10.

Once the reference parameters 22 are calculated by the processing unit 20 after entry via a suitable input device 15, the specific risk 25 for a particular patient can be calculated based on the individual's specific measured marker values, indicated at 30.

Figure 12A:
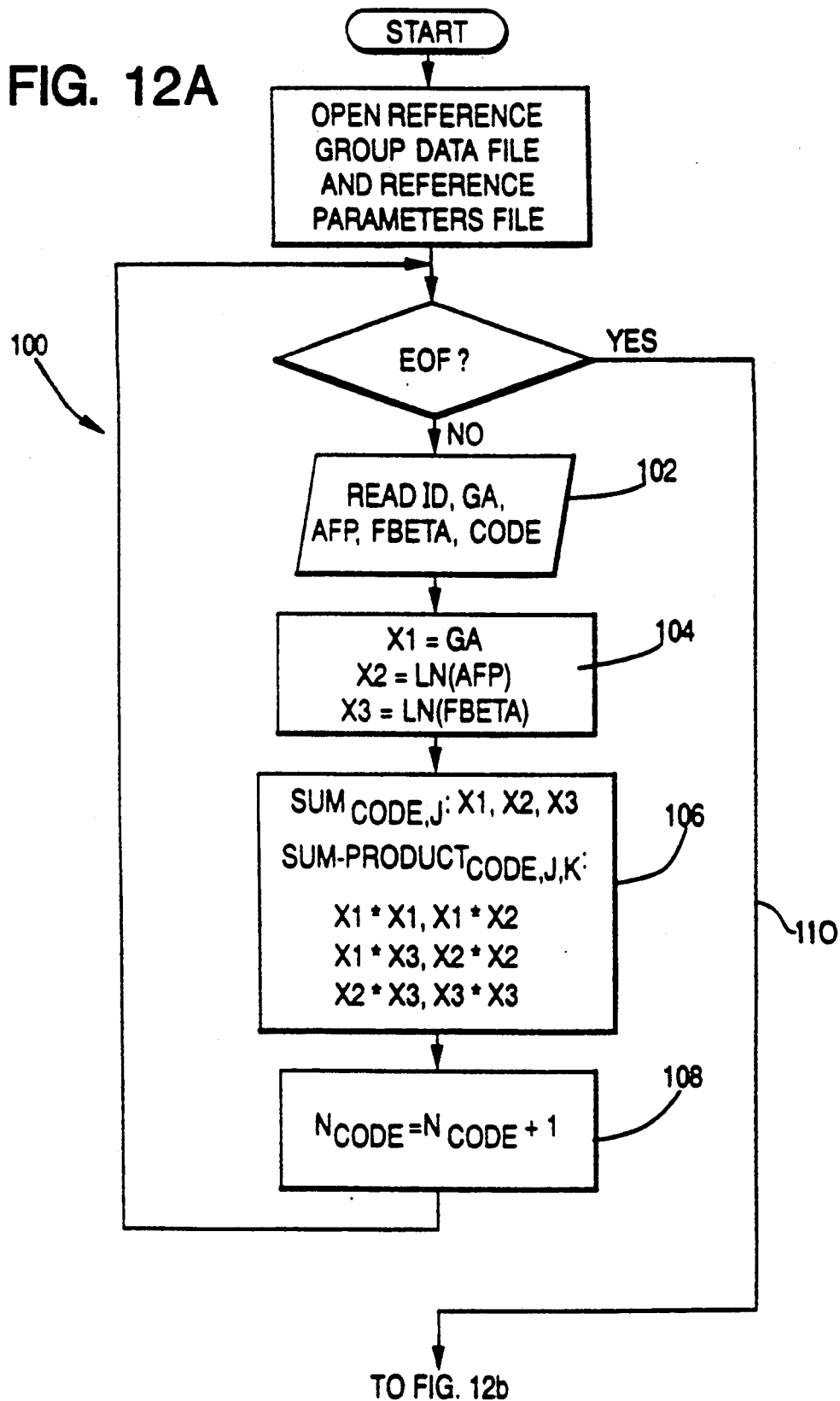
FIGS. 12a&b and 13a&b show a flowchart for a computer program for calculating reference parameters for use in conjunction with the determination of a patient's specific risk of carrying an affected fetus.
Figure 14:
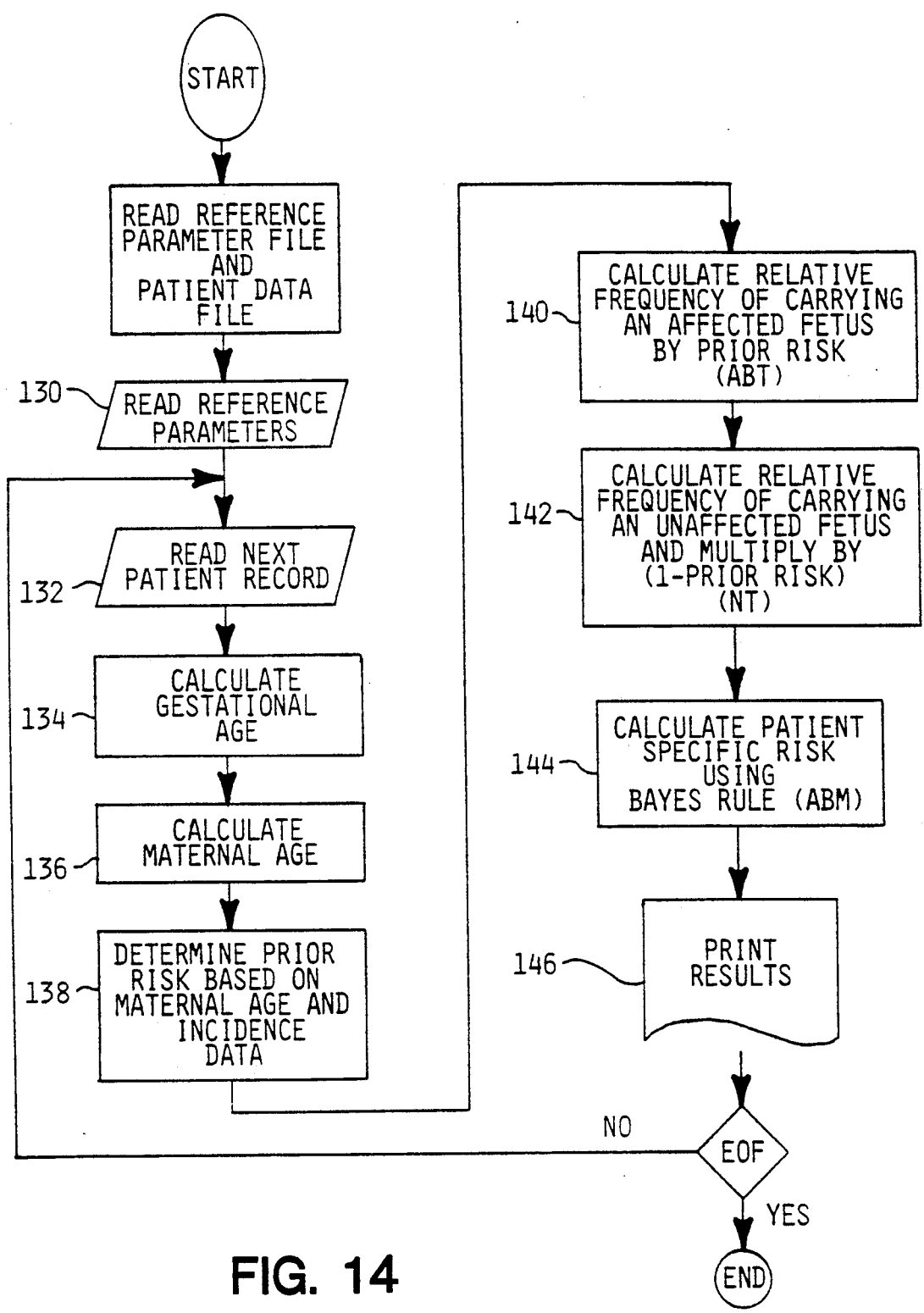
FIG. 14 shows a flowchart for a computer program utilizing the reference parameters calculated in the program shown in FIGS. 12a&b and 13a&b for determining the patient's specific risk of carrying an affected fetus.

The program for determining the reference parameters is shown in FIGS. 12a&b and 13a&b and the program for calculating specific risk is shown in FIG. 14.

With reference now to FIGS. 12a&b and 13a&b, in a first loop 100, the program reads in identification data ID, gestational age GA, quantities of AFP and free beta hCG and a CODE indicating whether the pregnancy is affected or unaffected by Trisomy 21 from a reference group in order to develop reference data. This is shown in step 102. In the flowchart, gestational age GA is denoted by variable $X_1$, the log of AFP is given by variable $X_2$ and the log of free beta is given by $X_3$, as shown in step 104. The sum and sum-product matrices are then determined or calculated as shown in step 106 based upon the quantities $X_1$, $X_2$ and $X_3$. The variable $N_{CODE}$ which counts the number of affected and unaffected cases in the reference group is then incremented. Once the loop is terminated, as shown by flow line 110, the means are then calculated through series of loops defined by the quantities I, J and K as indicated by reference numeral 112. In these loops, the covariance matrix is calculated utilizing the sum matrix defined in loop 100 and the sum product matrix calculated in loop 100. After these loops, a choice is made whether to pool or not to pool the covariance matrices for the affected and unaffected. This choice is inputted in steps 114, 116 and 118. If the choice is to pool, the covariances are pooled to form a pooled covariance matrix as given by step 120, the pooled covariance matrix is inverted resulting in the inverted pooled covariance matrix IPCM as shown at 122, and the means and the inverted pooled covariance matrix are saved in a file and printed out at steps 124 and 126. If the choice is not to pool the covariance matrices, then each of the two covariance matrices are inverted in steps 123 and 125 and the means and the inverted covariance matrices are saved in a file and printed out in steps 125 and 127. These quantities comprise the reference parameters for the calculation of a specific individual's risk of carrying an affected fetus.

Figure 12B:
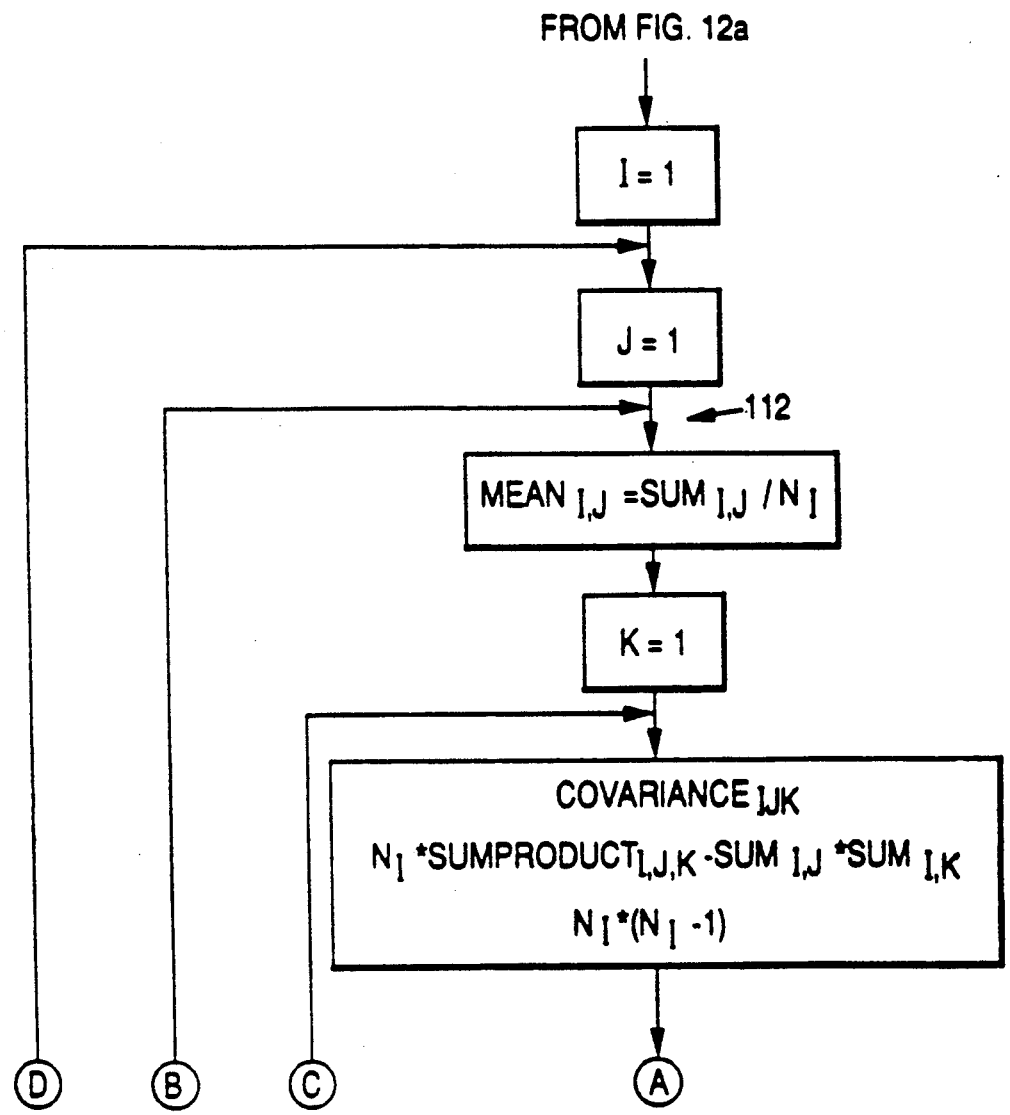
Figure 13A:
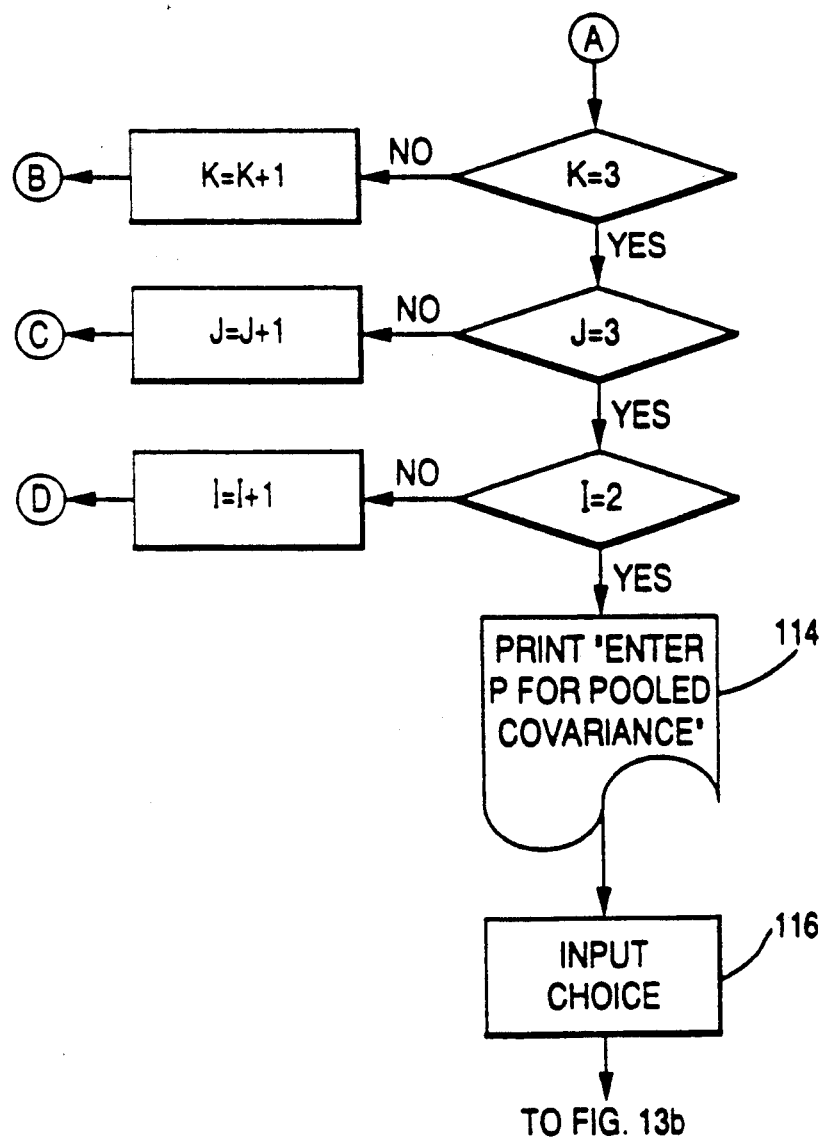
Figure 13B:
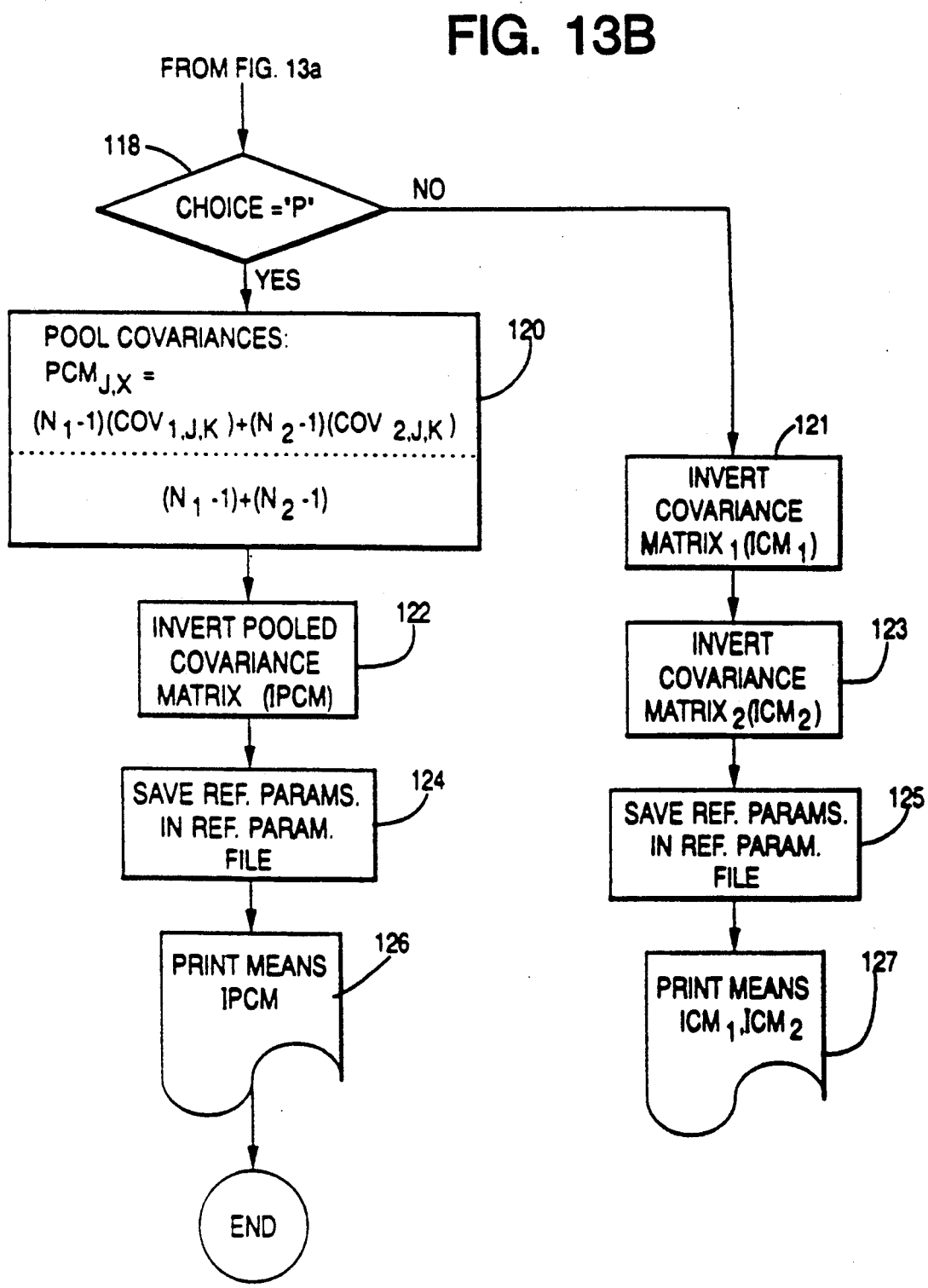

With reference to FIG. 14, the reference parameters determined during the execution of the program shown in FIGS. 12 and 13, the reference parameters comprising the means and the inverted pooled covariance matrix, are read in as shown at 130. The specific patient record, including the patient identification, the gestational age GA, AFP and free beta hCG are then read in as shown at 132. The gestational age is then calculated more specifically at 134, and a maternal age calculation is made at 136. At 138, the prior risk is determined based upon maternal age and incidence data. In the examples discussed below, the result of this calculation is the factor 1/800, a typical number.

At 140, the prior risk times the relative frequency of carrying an affected fetus (ABT) is determined, which is the numerator of the equations (1) or (2) discussed above. At 142, the relative frequency of carrying an unaffected fetus multiplied by (1-prior risk), (NT), is determined, which is the second factor in the denominator of equations (1) or (2) found above. At 144, the specific risk using Bayes Rule is determined, i.e., ABN = ABT/(ABT+NT). (Equations (1) and (2)). At 146, the results are printed, i.e., the patient's specific risk ABN and the patient identification number.

As will be apparent to a person of skill in the art, other statistical and mathematical techniques for calculating the reference parameters, other than a linear discriminant analysis procedure, can also be used.

According to a preferred embodiment of the present invention a maternal blood sample is taken from a patient. The maternal blood levels of free beta-hCG, and AFP (hereinafter referred to as "markers") are then measured by conventional analytical methods, including immunological methods known to the art. Although any of the known analytical methods for measuring the maternal blood levels of these markers will function in the present invention, as obvious to one skilled in the art, the analytical method used for each marker must be the same method used to generate the reference data for the particular marker. If a new analytical method is used for a particular marker, a new set of reference data, based on data developed with the method, must be generated.

A patient specific risk of carrying a fetus with Dow syndrome is then calculated using Bayes rule, the patient's a priori risk, and the relative frequencies for unaffected and affected pregnancies which are determined by incorporating the patient's quantitative levels of each marker along with the patient's gestational age, into the probability density functions developed for the reference data using multivariate discriminant analysis. To further increase detection efficiency, the log of the patient's quantitive levels of free beta-hCG and AFP, along with the patient's gestational age, are incorporated into the probability density functions developed for the reference data using multivariate discriminant analysis. The multivariate discriminant analysis can be performed on the commercially available computer program statistical package Statistical Analysis System (manufactured and sold by SAS Institute Inc.) or by other methods of multivariate statistical analysis or other statistical software packages known to those skilled in the art.

For the purposes of the discriminant analysis an assumption is made as to the prior probability of Down syndrome in the general unselected population. Generally, the prior probability is approximately 1 in 800. For the multivariate discriminant analysis a decision is made as to what risk cut-off level constitutes a positive test result. For example, if it is desirable to perform further diagnostic tests on a pregnant woman who has a 1 in 400 or greater possibility of carrying a Down syndrome fetus, then when the results of the discriminant analysis indicate that a pregnant woman has a 1 in 400 or greater possibility of carrying a Down syndrome fetus, the pregnant woman is considered to have a positive test result. If a positive test result is indicated, the patient should be counseled about further diagnostic tests to confirm the presence of Down syndrome.

As obvious to one skilled in the art, in any of the embodiments discussed above, changing the risk cut-off level of a positive or using different a priori risks which may apply to different subgroups in the population, could change the results of the discriminant analysis for each patient.

The present invention is not limited to the embodiments discussed above but rather includes all of the possible embodiments and combination of markers disclosed in the following examples.

EXAMPLE 1

Over 400 patient samples were utilized to study the relationship of fetal Down syndrome to the maternal blood levels of free beta-hCG in conjunction with maternal serum AFP (MSAFP), UE, and intact hCG. These samples included 25 maternal blood samples from pregnant women known to be carrying fetuses with Down syndrome and control samples matched to the affected cases.

For each blood sample quantitative levels of AFP, the intact hCG molecule, free beta-hCG, and UE (hereinafter each is referred to as a "Marker") were determined by the following assay techniques:

| Marker | Assay Technique |
| --- | --- |
| MSAFP | Enzyme linked immunosorbent assay (ELISA) |
| UE | Radioimmunoassay |
| Intact hCG | Bead type ELISA |
| free beta-hCG | ELISA |

The level of each Marker became a variable in the stepwise discriminant procedure and the linear discriminant procedure on the commercially available computer software statistical package Statistical Analysis System (SAS Institute Inc.) to generate a set of reference data. The ratio of free beta hCG to the intact hCG molecule and the patient's gestational age were also incorporated as variables. The stepwise discriminant procedure determined that all of the variables could be incorporated into the linear discriminant procedure. The linear discriminant procedure was then performed on each variable separately and on different combinations of variables. The results of these discriminant analyses are summarized in the chart below. Sensitivity is the percentage of fetal Down syndrome cases which show a positive test result. False positives is the percentage of normal fetuses which show a positive test result.

| VARIABLE | SENSITIVITY | FALSE POSITIVES |
| --- | --- | --- |
| MSAFP | 15.4% | 4.2% |
| UE | 15.4% | 2.8% |
| Intact hCG | 37% | 8.6% |
| MSAFP, UE Intact hCG | 50.0% | 7.2% |
| free beta-hCG + Intact hCG | 60.0% | 8.5% |
| Composite w/o ratio | 76% | 5.3% |
| Composite w/o UE | 76% | 5.3% |
| Composite | 80% | 4.3% |
| Composite w/o free beta-hCG | 60.0% | 5.3% |
| *log intact hCG + (log free beta-hCG + intact hCG) | 68% | 7.6% |
| *log intact hCG, log MSAFP + (log free beta-hCG + intact hCG) | 88% | 7.4% |

| VARIABLE | SENSITIVITY | FALSE POSITIVES |
| --- | --- | --- |
| Composite = MSAFP + free beta-hCG + Intact hCG + UE + Ratio | | |

Gestational age is incorporated along with each variable Risk cut-off level = 1 in 400 except (*) which is 1 in 365.

As obvious to one skilled in the art, changing the risk cut-off level of a positive, or use of different a priori risks which may apply to different subgroups in the population, will change the results of the discriminant procedure for the patient.

EXAMPLE 2

Over 550 patient samples were utilized to study the relationship of fetal Down syndrome to the maternal blood levels of free beta-hCG Initially 29 samples from pregnant women known to be carrying fetuses with Down syndrome and 520 unaffected samples matched for gestational age (same week), maternal age (within 3 years) and freezer storage time (within one month) were analyzed. All samples were from singleton, non-diabetic, white gravid women.

In order to avoid training set bias in estimates of screening efficiency, the concept of a validation set was used. A validation set is a set of data independent of the reference data set. The results from patients in the validation set are not used in establishing reference data. Rather, results from patients in the validation set are compared to the reference data set to determine screening efficiency. This second trisomy 21 (55 cases total) and a randomly selected group of 159 control samples. The control samples were similarly drawn from singleton, non-diabetic, white gravid women.

The total study consisted of 4388 determinations on 7 different assays of the maternal blood levels of the markers as set forth below:

| Marker | Assay |
| --- | --- |
| MSAFP | ELISA (enzyme linked immunosorbent assay) |
| Intact hCG | ELISA |
| Intact hcg + free beta-hCG | ELISA |
| free beta-hCG | RIA (radio immunoassay) |
| free alpha-hCG | RIA |
| UE | 2 methods, Enzyme Immunoassay & RIA |

The level of each Marker became a variable in the stepwise discriminant procedure and the linear discriminant procedure on the commercially available computer software statistical package Statistical Analysis System (SAS Institute Inc.) to generate a set of reference data. Gestational age was also incorporated as a variable. The linear discriminant procedure was then performed on each variable separately and on different combinations of variables. Patients were classified as being affected or unaffected based on a Down syndrome risk cut-off of 1 in 365. Unaffected cases that were classified as affected were considered false positive. Each patient's risk of Down syndrome was calculated using Bayes, rule, the multivariate normal probability density functions for affected and unaffected cases, and a general a priori risk of 1 in 800. A pooled covariance matrix was used for each probability density function.

The results found in Tables 1 through 3, shown in FIGS. 1-3, relate to the initial study set. Results in tables 5-7, FIGS. 5-7, are based on the classification of patients in the validation set. Table 4, shown in FIG. 4, and FIGS. 8 and 9 are based on the initial study set and all affected cases.

The results from the assay procedures were analyzed to determine whether there existed significant differences in the levels of each marker between affected and unaffected cases. Table 1 (FIG. 1) indicates that affecteds were significantly different from unaffected in all but U.E. Additionally, the false positive rate and detection efficiency of each marker was determined as shown in Table 2 (FIG. 2). The highest detection efficiency was achieved with an hCG assay measuring both the intact molecule and the free beta subunit. A further enhancement in detection efficiency was observed by combining individual markers into composites. The composite containing the hCG assay, which measured both the intact hCG molecule and the free beta subunit of hCG, produced the highest detection efficiency among the composites as shown in Table 3 (FIG. 3).

The evaluation of the beta and alpha subunit of hCG individually showed that no significant differences existed between affected and unaffected cases for the alpha subunit ($p=0.23$) while a significant increase in the B subunit was observed in affecteds ($p=0.001$). As generally known in the art, p measures the strength of evidence in scientific studies by indicating the probability that a result at least as extreme as that observed would occur by chance. The lower the p value the stronger the evidence that the observation is not a chance occurrence.

Figure 9:
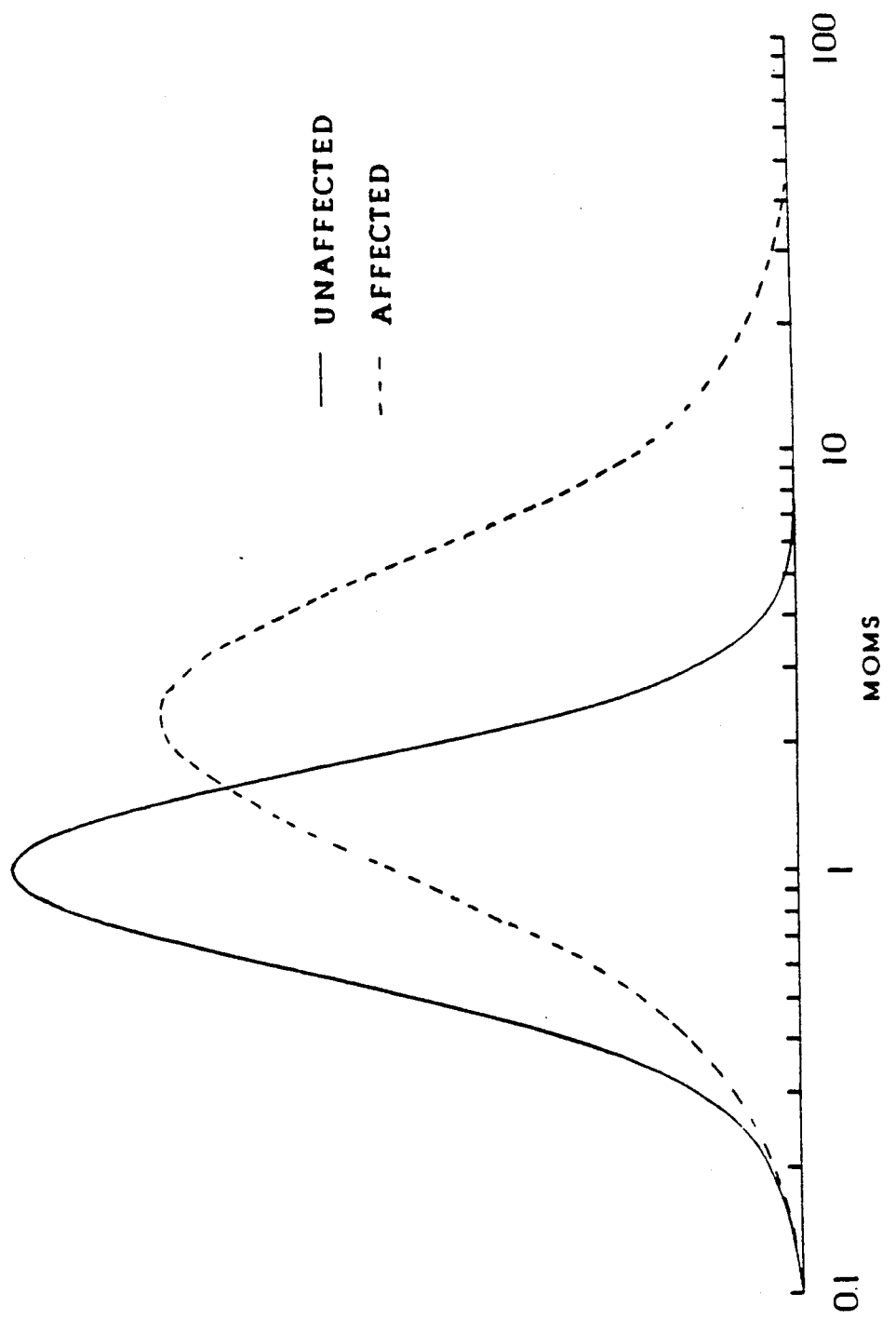
FIG. 9, referred to in Example 2, shows the distributions of free beta subunit of hCG levels.

FIG. 8 shows the 10th, 50th and 90th percentiles of free beta-hCG by gestational age. A continuing downward trend by gestational age in unaffected pregnancies is observed. Analysis of free beta-hCG levels in cases of fetal Down syndrome, as shown in Table 4 (FIG. 4), reveals that 86% fall above the median of unaffecteds.

The levels of free beta-hCG in both the affected and unaffected cases fit a log Gaussian distribution ($p=0.78$ and 0.86). FIG. 9 illustrates these distributions. Table 5 (FIG. 5) provides detection efficiency data on the free beta-hCG subunit and the free alpha-hCG subunit individually. The high detection efficiency of free beta-hCG is shown in Table 5.

An even higher detection efficiency was achieved with a composite of AFP and free beta-hCG. By incorporating the log of the level of free beta-hCG and the log of the level of MSAFP into the linear discriminant procedure on the commercially available computer software statistical package Statistical Analysis System (SAS Institute Inc.), as described above, a superior detection efficiency was achieved as shown in Table 6 (FIG. 6).

A high detection efficiency would also be achieved using the level of free beta-hCG and the level of AFP, as opposed to the log of each.

Further analysis of the data noted that both AFP and free beta-hCG are independent of maternal age ($p=0.8394$ and 0.5214 using Kruskal-Wallis tests across four different maternal age groups for AFP and free beta-hCG respectively, (ages=30, 31-35, 36-40, and 40). Additionally the correllation (r) of the levels of free beta-subunit of hCG and AFP was not significantly different from zero ($r=0.04$, $p=0.39$ and $r=-0.06$, $p=0.81$ for unaffected and affected cases respectively).

The fundamental observation found in our data confirms the fact that the free beta-hCG subunit contributes the highest detection efficiency for Down syndrome. In fact, the use of an assay measuring solely free beta-hCG produced a detection efficiency and false positive rate 65.4% and 5.2% respectively. These rates are comparable to those reported by others utilizing a combination of three assays. Thus, as previously set forth, reducing the number of assays is an advantage of the present invention.

Our findings on the contribution of free beta-hCG a based on the following: (a) the single best contributor to detection efficiency for Down syndrome was an assay for free beta-hCG, (b) an assay for the intact hCG molecule yields substantially lower detection rates, (c) an assay which measures a combination of the intact hCG molecule and free beta-hCG yields a higher detection efficiency than an assay measuring the intact hCG molecule alone.

It is established that the risk of fetal Down syndrome increases with maternal age. Therefore, as described above, to produce patient-specific risks for clinical use of the present invention a maternal age specific a priori risk is incorporate into the multivariate discriminant analysis procedure. Since both AFP and free beta-hCG levels are independent of maternal age, we have analyzed our data to see how many unaffected and affected women would have positive results given an a priori risk for each individual age. The foregoing information was used to project, based upon the maternal age distribution of live births in the United States, the false positive and sensitivity rate for comprehensive nationwide screening within the United States. As shown in Table 7 (FIG. 7) the projections indicate that it is possible to achieve a detectic rate of 80%, with 5% false positives.

The samples described in Example 2 were further analyzed to discover the detection efficiency of other combinations of the markers. More particularly, the linear discriminant procedure of Example 2, with the same risk cut-of and a priori risk level, was performed on different combinations of the markers, multiples of the median (MOM) for the marker and logs of the markers, with and without the incorporation of gestational age. The linear discriminant procedure was performed using both the reference data and the validation data. The results are summarized in Table 8 in FIG. 10.

EXAMPLE 3

The following example illustrates the preparation of a one step free beta-hCG assay and a two step free beta hCG assay and their use in the method of the present invention.

PREPARATION OF A ONE STEP FREE BETA-hCH ASSAY

1. A ninety-six well microtiter plate is coated with a "catching" antibody that is specific to the free beta subunit of the human chorionic gonadotropin (hCG) molecule. The antibody may be either monoclonal or polyclonal. The concentration of antibody used to coat the plate is 0.8 micrograms per well but could be different, if desired. The plate is incubated at 4° C. for at least 16 hours.

2. The plate is washed with a phosphate buffered saline solution of pH 7.2 that contains 0.05% Tween 20. Other suitable wash buffers may be employed The plate is then "blocked" with a solution containing 3% hydrolyzed animal protein and 0.05% Tween 20 in a phosphate buffered saline solution of pH 7.2. Other solutions, familiar to those skilled in the art, such as a 1% bovine serum albumin solution, may be used. Three hundred microliters of the blocking solution is added to each well and the plate is allowed to incubate for on hour at ambient temperature. Other blocking procedures are also viable, e.g. "glazing".

3. The plate is then washed, as described earlier, and 100 microliters of assay buffer containing a biotinylated antibody specific to the free beta subunit of hCG is added to each well. The assay buffer used is 3% hydrolyzed animal protein and 0.05% Tween 20 in a phosphate buffered saline solution of pH 7.2, but may be any of a number of suitable solutions known to those skilled in the art. The antibody may be monoclonal or polyclonal and, depending on the preference of the operator, may be conjugated to a substance other than biotin, such as horseradish peroxidase or alkaline phosphatase. The concentration of the antibody in the assay buffer may be adjusted to obtain optimal absorbance values.

4. Twenty microliters of sample is then added to each well. The sample may be: assay buffer, run as blank to verify the performance of the assay; a solution of free beta hCG used to standardize values of unknown samples; or a serum sample from second trimester gravid woman. The plate is vortexed for 30 seconds and then placed on a rotator @ 200 rpm, where it incubates for 30 minutes at ambient temperature.

5. The plate is then washed as described previously. One hundred microliters of assay buffer containing streptavidin conjugated to horseradish peroxidase is then added to each well. This step is not required if the second antibody used is conjugated to a substance other than biotin. The concentration of streptavidin-peroxidase in assay buffer is 2.0 micrograms per milliliter. The plate is placed on a rotator @ 200 rpm for 5 minutes at ambient temperature.

6. The plate is then washed as described previously. One hundred microliters of an o-phenylendiamine substrate solution is added to each well. This substrate solution may alternatively be any one of a number appropriate dyes known to those skilled in the art and depends upon what substance is conjugated to the second antibody. The plate is placed on a rotator @ 200 rpm and incubated at ambient temperature in the dark for 8 minutes.

7. One hundred microliters of dilute (1.0N) sulfuric acid is then added to each well to stop the reaction of the substrate.

8. The absorbance of each well is determined spectrophotometrically at 492 nm.

Preparation of a Two-step beta-hCG Assay

1. A ninety-six well microtiter plate is coated with a "catching" antibody that is specific to the free beta subunit of the human chorionic gonadotropin (hCG) molecule. The antibody may be either monoclonal or polyclonal. The concentration of antibody used to coat the plate is 0.8 micrograms per well but may be different, if desired. The plate is incubated at 4° C. for at least 16 hours.

2. The plate is washed with a phosphate buffered saline solution of pH 7.2 that contains 0.05% Tween 20. Other suitable wash buffers may be employed The plate is then "blocked" with a solution containing 3% hydrolyzed animal protein and 0.05% Tween 20 in a phosphate buffered saline solution of pH 7.2. Other solutions, familiar to those skilled in the art, such as a 1% bovine serum albumin solution, may be used. Three hundred microliters of the blocking solution is added to each well and the plate is allowed to incubate for one hour at ambient temperature. Other blocking procedures, such as "glazing," may be employed.

3. The plate is then washed, as described earlier, and 100 microliters of an assay buffer is added to each well. The assay buffer used is 3% hydrolyzed animal protein and 0.05% Tween 20 in a phosphate buffered saline solution of pH 7.2, but may be any of a number of suitable solutions known to those skilled in the art.

4. Twenty microliters of sample is then added to each well. The sample may be: assay buffer, run as the blank to verify the performance of the assay; a solution of free beta hCG used to standardize values of unknown samples; or a serum sample from a second trimester gravid woman. The plate is vortexed for 30 seconds and then placed on a rotator @ 200 rpm, where it incubates for 30 minutes at ambient temperature 5. The plate is then washed, as described previously, and 100 microliters of assay buffer containing a biotinylated antibody specific to the free beta subunit of hCG is added to each well. The antibody may be monoclonal or polyclonal and, depending on the preference of the operator, may be conjugated to a substance other than biotin, such as horseradish peroxidase or alkalinephosphatase. The concentration of the antibody may be adjusted to obtain optimal absorbance values. The plate is vortexed for 30 seconds and then placed on a rotator @ 200 rpm, where it incubates for 30 minutes at ambient temperature.

6. The plate is then washed as described previously. One hundred microliters, of assay buffer containing streptavidin conjugated to horseradish peroxidase is then added to each well. This step is not required if the second antibody used is conjugated to a substance other than biotin The concentration of streptavidin-peroxidase in assay buffer is 2.0 micrograms per milliliter The plate is placed on a rotator @ 200 rpm for minutes at ambient temperature.

7. The plate is then washed as described previously. One hundred microliters of an o-phenylenediamine solution is added to each well. This substrate solution may alternatively be any one of a number appropriate dyes known to those skilled in the art and depends upon what substance is conjugated to the second antibody. The plate is placed on a rotator @ 200 rpm and incubated at ambient temperature in the dark for 8 minutes.

8. One hundred microliters of dilute (1.0N) sulfuric acid is then added to each well to stop the reaction of the substrate.

9. The absorbance of each well is determined spectrophotometrically at 492 nm.

These two assays were used in carrying out the method of the present invention. One hundred seventy eight (178) patient samples were utilized to study the relationship of fetal Down syndrome to the maternal blood levels of free beta-hCG. Twenty six (26) samples from pregnant women known to be carrying fetuses with Down syndrome and 152 unknown unaffected samples were analyzed All samples were from singleton, non-diabetic, white gravid women.

The patient samples were then analyzed for quantitative levels of MSAFP, by an ELISA assay, and levels of free beta-hCG by the one step assay and the two step assay independently. The level of MSAFP and the level of free beta-hCG by each assay then became a variable in the linear discriminant procedure on the commercially available computer software statistical package Statistical Analysis System to generate a set of reference data. The patient's gestational age was also incorporated as a variable in the discriminant procedure. The results of these discriminant analyses, for all gestational ages, and for gestational ages between 14 and 16 weeks are summarized below.

|  | False Positive | Detection Efficiency | Controls | Affected |
|---|---|---|---|---|
| ALL WEEKS | | | | |
| Log (beta-1) | 6.6% | 69.2% | 152 | 26 |
| Log (beta-1) + Log (AFP) | 5.9% | 72.0% | 152 | 25 |
| Log (beta-2) | 8.2% | 33.3% | 138 | 18 |
| Log (beta-2) + Log (AFP) | 10.1% | 64.7% | 138 | 17 |
| Log (beta-2)* | 9.6% | 33.3% | 136 | 18 |
| Log (beta-2) + Log (AFP)* | 10.3% | 52.9% | 136 | 17 |
| Weeks 14–16 | | | | |
| Log (beta-1) | 5.8 | 68.4% | 104 | 19 |
| Log (beta-1) + Log (AFP) | 4.8% | 73.7% | 104 | 19 |
| Log (beta-2) | 7.1% | 45.4% | 98 | 11 |
| Log (beta-2) + Log (AFP) | 9.2% | 63.6% | 98 | 11 |
| Log (beta-2)* | 10.4% | 54.6% | 96 | 11 |
| Log (beta-2) + Log (AFP)* | 8.3% | 63.6% | 96 | 11 |

Note: All analyses included gestational age
*In the analyses with a * next to them 2 outliers with values of 260 and 316 were removed.
The suffix -1 means one-step procedure, -2 means two-step procedure.
Detection Efficiency refers to the percentage of fetal Down Syndrome cases which show a positive test result.
False Positive refers to the percentage of normal fetuses which show a positive test result.
Controls refers to the number of unaffected samples analyzed.
Affected refers to the number of affected samples analyzed.

Using a combination of the one-step assay for free-B and AFP yields the highest detection efficiency with the lowest false positive rate for all weeks of gestation and for 14–16 weeks of gestation.

Our findings support the performance of Down syndrome screening in a feasible and effective fashion within a prenatal serum screening protocol which includes: (a) non-invasive techniques (b) high detection efficiency with low false positive rates, (c) use of markers which are largely independent of each other (d) absence of unwieldy restrictions in blood sampling (time of day, diet, personal habits, etc.) and (e) compatibility with other prenatal screening services.

Our results indicate that it is possible to achieve higher detection rates in Down syndrome screening while conducting fewer biochemical analyses than proposed by others. The use of only the most effective markers in Down syndrome screening can serve to provide non-invasive screening information during the early antenatal period to the highest proportion of families affected by this most common cause of severe mental retardation.

As obvious to one skilled in the art changing the risk cut-off level of a positive, or using different a priori risks which may apply to different subgroups in the population, will change the results of the discriminant procedure for the patient.

EXAMPLE 4

This example illustrates the use of the method of the present invention in screening for Down syndrome during the first trimester of pregnancy. Maternal serum samples from 150 patients were utilized. Each patient was carrying a fetus that, at the time the sample was taken, was between 9 and 13 weeks of gestational age. 139 of the patients were carrying a fetus without Down syndrome, referred to herein as "controls" and 11 patients were carrying a fetus with Down syndrome. Each of the patients was a non-diabetic, white, woman with a singleton pregnancy.

Figure 15:
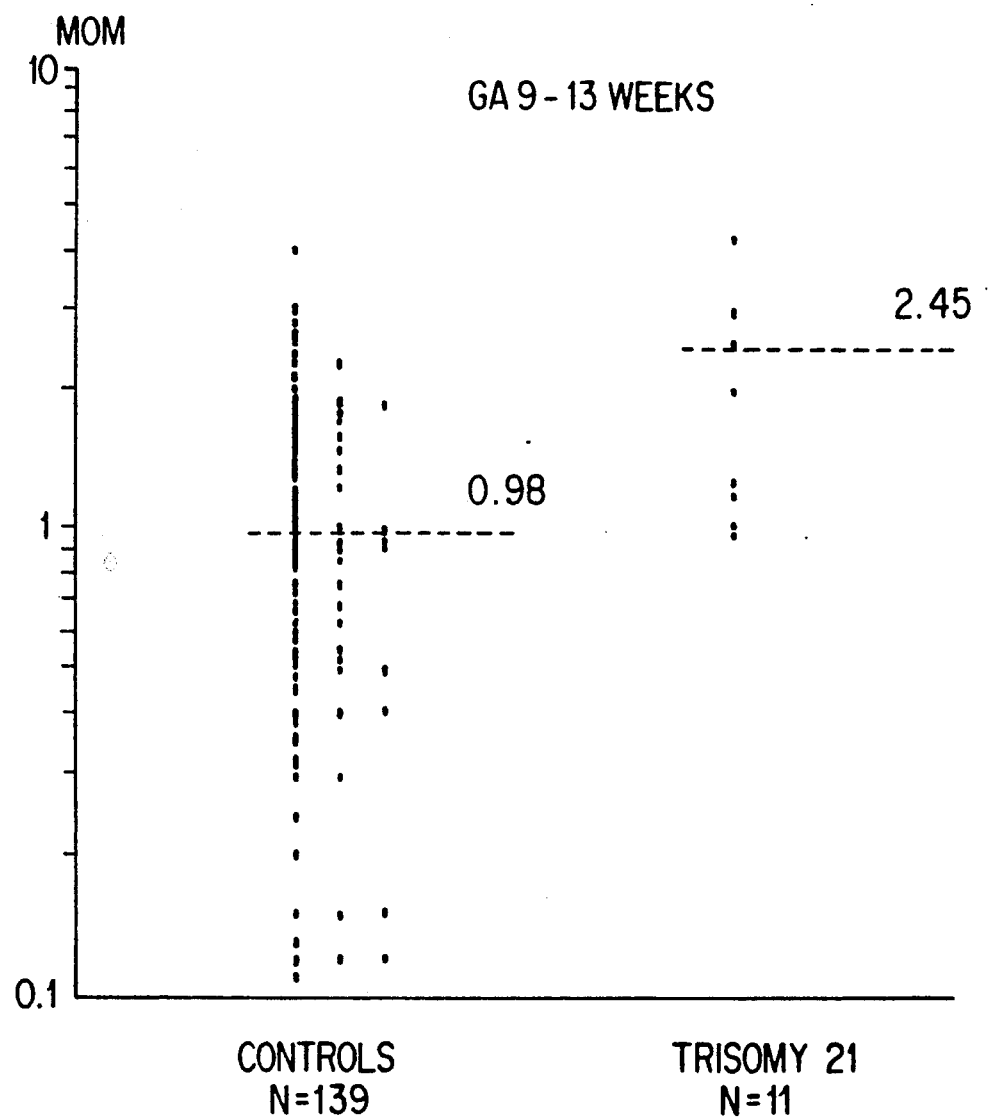
FIG. 15, referred to in Example 4, shows the distribution of free beta levels in patient samples.

The level of free beta in each of the 150 maternal serum samples was analyzed utilizing the two step free beta hCG assay described in Example 3. The results of this analysis are shown graphically in FIG. 15. As shown in FIG. 15, the median level of free beta in the maternal serum of patients carrying a fetus with Down syndrome was 2.45 MOM (multiples of the median) greater than the median level of free beta in the maternal serum of the controls. This level of free beta in patients carrying a fetus with Down syndrome is significantly greater than the level of free beta in the controls. Thus, the free beta protein is significantly elevated in the first trimester when Down syndrome is present.

EXAMPLE 5

This example also illustrates the use of the method of the present invention in screening for Down syndrome during the first trimester of pregnancy. Maternal serum samples from 277 patients were utilized. Each patient was carrying a fetus that, at the time the sample was taken, was between 7 and 13 weeks of gestational age. 264 of the patients were carrying a fetus without Down syndrome, referred to herein as "controls" and 13 patients were carrying a fetus with Down syndrome. Each of the patients was a non-diabetic, white, woman with a singleton pregnancy.

Figure 16:
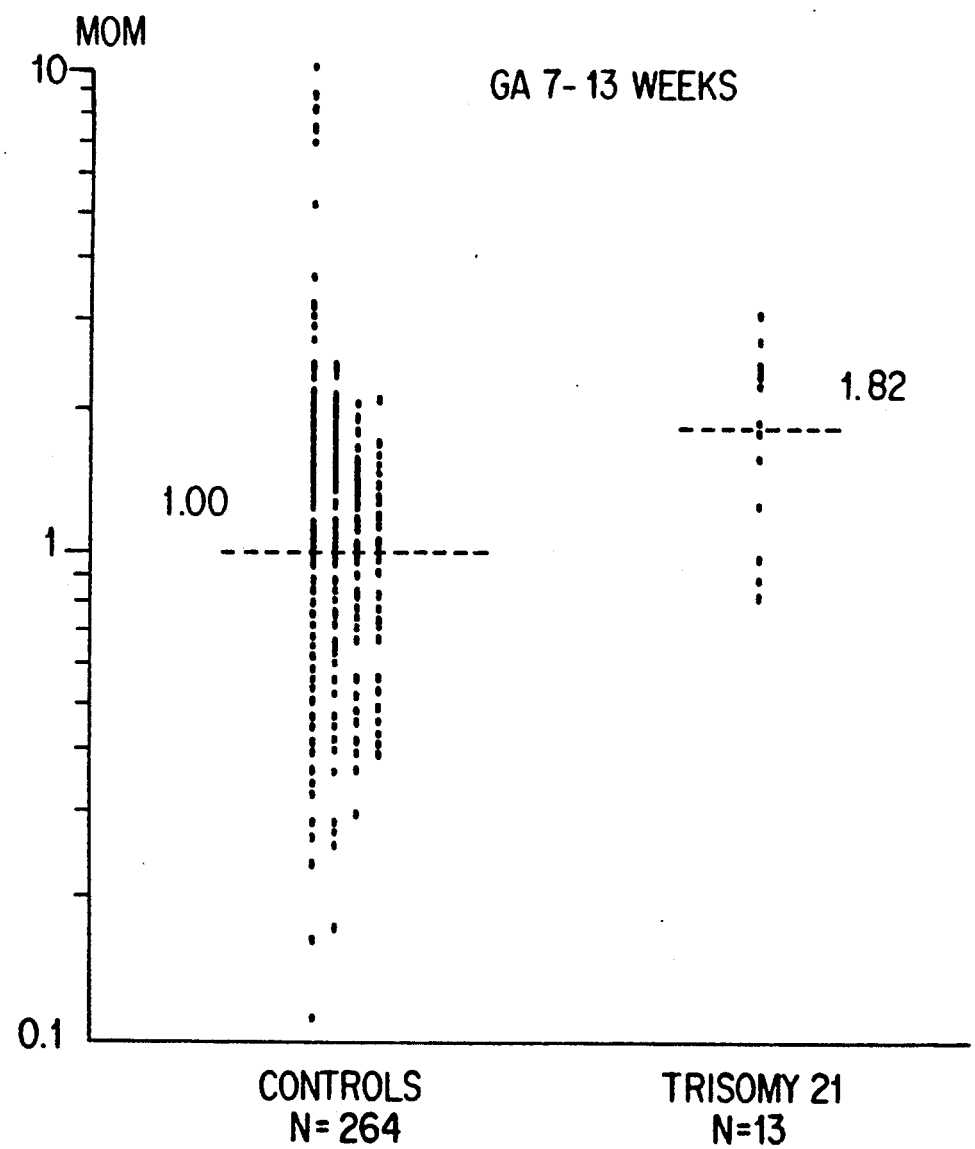
FIG. 16, referred to in Example 5, shows the distribution of free beta levels in patient samples.

The level of free beta in each of the 277 maternal serum samples was analyzed utilizing the two step free beta hCG assay described in Example 3. The results of this analysis are shown graphically in FIG. 16. As shown in FIG. 16, the median level of free beta in the maternal serum of patients carrying a fetus with Down syndrome was 1.82 MOM (multiples of the median) greater than the median level of free beta in the maternal serum of the controls. This level of free beta in patients carrying a fetus with Down syndrome is significantly greater than the level of free beta in the controls. Thus, the free beta protein is significantly elevated in the first trimester when Down syndrome is present.

EXAMPLE 6

This example further illustrates the use of the method of the present invention in screening for Down syndrome during the first trimester of pregnancy. Maternal serum samples were drawn from 392 patients who had chosen to undergo a chorionic villus sample (CVS) procedure. The CVS procedure is a clinical technique wherein a sample of chorionic villi is obtained for chromosomal analysis. The serum samples utilized in this example were drawn from the patients prior to the patients undergoing the CVS procedure. Usually, this technique is utilized with patients 35 years old, or older, a group that is known to have a higher incidence of carrying a fetus with Down syndrome, or utilized with patients having a family history of chromosomal abnormalities.

Each patient was carrying a fetus that, at the time the sample was taken, was between 9 and 13 weeks of gestational age. 386 of the patients were carrying a fetus without Down syndrome, referred to herein as "controls" and 6 patients were carrying a fetus with Down syndrome. Each of the patients was a non-diabetic, white, woman with a singleton pregnancy.

Figure 17:
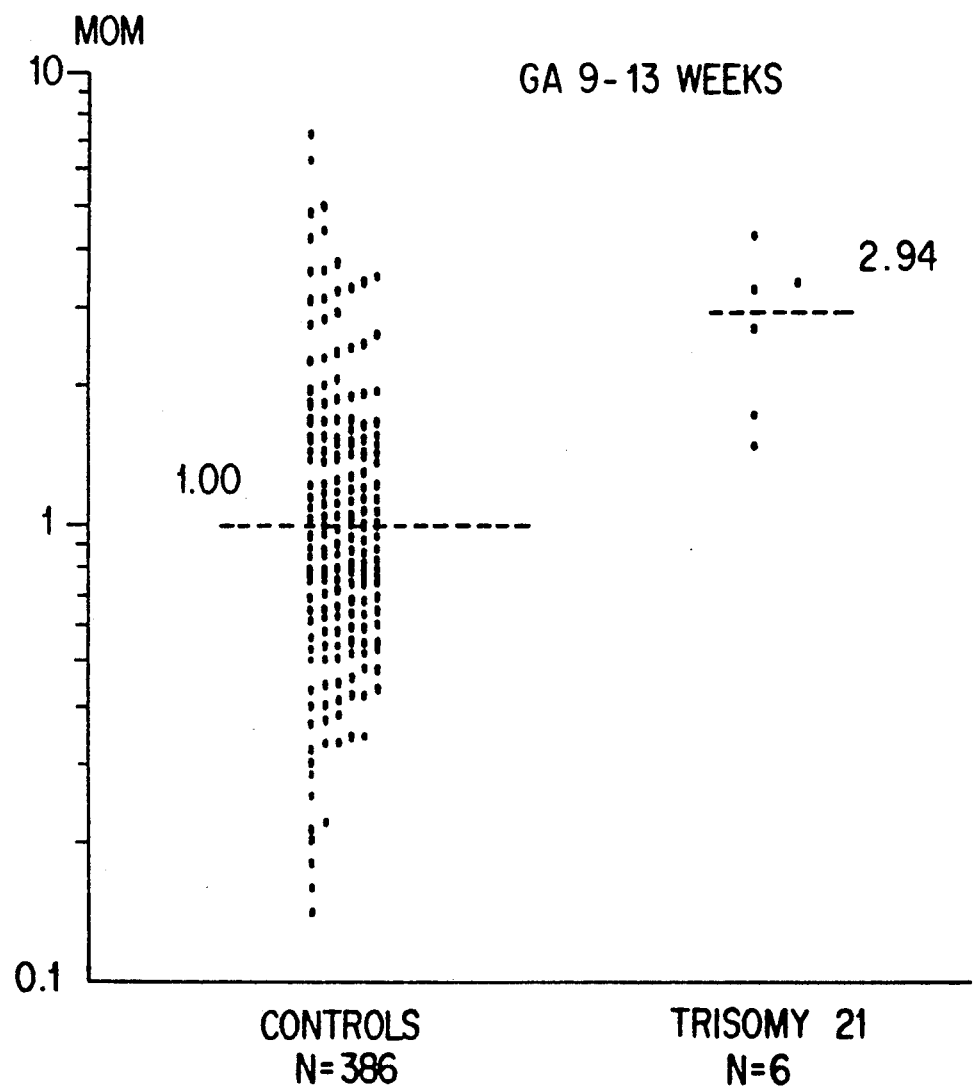
FIG. 17, referred to in Example 6, shows the distribution of free beta levels in patient samples.

The level of free beta in each of the 392 maternal serum samples was analyzed utilizing the two step free beta hCG assay described in Example 3. The results of this analysis are shown graphically in FIG. 17. As shown in FIG. 17, the median level of free beta in the maternal serum of patients carrying a fetus with Down syndrome was 2.94 MOM (multiples of the median) greater than the median level of free beta in the maternal serum of the controls. This level of free beta in patients carrying a fetus with Down syndrome is significantly greater than the level of free beta in the controls. Thus, the free beta protein is significantly elevated in the first trimester when Down syndrome is present. The Examples further illustrate that the method of the present invention, as described herein, may be utilized to non-invasively screen for Down syndrome during the first or second trimester of pregnancy. As used herein, the first trimester of pregnancy refers to the time period prior to 14 weeks of gestational age. Similarly, the second trimester of pregnancy refers to the time period between 14 and 26 weeks of gestational age.

For example, a laboratory could generate a set of gestational week specific reference data containing the levels of free beta in maternal serum samples obtained during the first trimester of pregnancy. This reference data can be generated in a manner comparable to the manner set forth in the Examples.

To screen for fetal Down syndrome, the laboratory would measure and compare the level of free beta in a blood sample obtained from a patient during the first trimester of pregnancy to the reference data to determine whether the patient is at sufficient risk of carrying a fetus with Down syndrome to warrant further testing. As set forth herein, this determination by the laboratory requires a comparison of the patient's aposteriori (after screening) risk of carrying a fetus with Down syndrome with an established cut-off level which reflects the risk to the patient and fetus of an invasive procedure to obtain fetal cells for chromosomal analysis.

A laboratory could decide to use a multiples of the median approach to determine a positive screening result. For example, using the data set forth in Example 4 as a set of reference data, the reference data would indicate that the median level of free beta is 2.45 times greater in women carrying Down syndrome fetuses than in women carrying unaffected fetuses. Using a multiples of the median approach to screening, if the level of free beta in the patient's sample is greater than a chosen cut-off level such as 2.5 multiples of the median greater than the level of free beta in the controls, the laboratory would recommend that the woman undergo further invasive testing to diagnose whether her fetus has Down syndrome.

It should be noted that this screening method, relying on a Multiples of the Median approach for a single analyte, may not be as accurate as a screening procedure utilizing multiple analytes and a multivariate discriminant analysis approach, such as that described in Example 1.

Accordingly, it should be clearly understood that the present invention includes all modifications falling within the scope of the following claims.

I claim:

1. A method for screening a pregnant woman to determine if said pregnant woman's risk of carrying a fetus with Down syndrome warrants further testing comprising:
   selecting a risk cut-off level that will determine whether said pregnant woman should be offered further testing;
   assigning a prior risk level for said pregnant woman's risk of carrying a fetus with Down syndrome;
   measuring said pregnant woman's blood during the first trimester of pregnancy for free beta (human chorionic gonadotropin (HCG) level; and
   comparing said level of free beta (HCG) to a set of reference data, containing reference values of the blood level of free beta (HCG) during the first trimester of pregnancy in: (1) pregnant women carrying Down syndrome fetuses and (2) pregnant women carrying normal fetuses said comparison in conjunction with said prior risk being indicative of whether said pregnant woman's risk of carrying a fetus with Down syndrome is greater than the selected risk cut-off level wherein a higher level of free beta (HCG) is indicative of a higher probability of carrying a fetus with Down syndrome.

2. The method of claim 1 wherein the free beta (HCG) is a variant form of free beta (HCG).

3. The method of claim 2 where the free beta (HCG) is nicked free beta (HCG).

4. A method for screening a pregnant woman to determine if said pregnant woman's risk of carrying a fetus with Down syndrome warrants further testing comprising:
   selecting a risk cut-off level that will determine whether said pregnant woman should be offered further testing;
   assigning a prior risk level for said pregnant woman's risk of carrying a fetus with Down syndrome;
   measuring said pregnant woman's blood during the second trimester of pregnancy for free beta (human chorionic gonadotropin (HCG) level; and
   comparing said level of free beta (HCG) to a set of reference data, containing reference values of the blood level of free beta (HCG) during the second trimester of pregnancy in: (1) pregnant women carrying Down syndrome fetuses and (2) pregnant women carrying normal fetuses said comparison in conjunction with said prior risk being indicative of whether said pregnant woman's risk of carrying a fetus with Down syndrome is greater than the selected risk cut-off level wherein a higher level of free beta (HCG) is indicative of a higher probability of carrying a fetus with Down syndrome.

5. The method of claim 4 wherein the free beta (HCG) is a variant form of free beta.

6. The method of claim 5 wherein the free beta (HCG) is nicked free beta (HCG).

7. A method for determining the risk that a pregnant woman is carrying a fetus with Down syndrome comprising: measuring said pregnant woman's maternal blood level of a fragment of free beta (human chorionic gonadotropin (HCG)) during the second trimester of pregnancy and comparing the measurement of said level of the fragment of free beta (HCG) to reference data containing reference values of the level of the fragment of free beta (HCG) during the second trimester of pregnancy in: (1) pregnant women carrying Down syndrome fetuses and (2) pregnant women carrying normal fetuses, said comparison being indicative of the pregnant woman's risk wherein a higher level of the fragment of free beta (HCG) is indicative of a higher probability of carrying a fetus with Down syndrome.

* * * * *